United States Patent [19]

Kawashima et al.

[11] Patent Number: 5,288,487

[45] Date of Patent: Feb. 22, 1994

[54] HUMAN MONOCYTE-MACROPHAGE-CSF PREPARATIONS

[75] Inventors: Takuji Kawashima, Kawasaki; Nobuya Yanai, Tokyo; Muneo Yamada, Zama; Hajime Yokota; Kunio Ujiie, both of Tokyo; Katsuo Yoshida, Higashiyamato; Shinya Suzu, Shimotsuga; Fumimaro Takaku, Tokyo; Kazuo Motoyoshi, Ohmiya; Nobuhiro Yamada, Tokyo, all of Japan

[73] Assignee: Morinaga Milk Industry Co., Ltd., Tokyo, Japan

[21] Appl. No.: 789,431

[22] Filed: Nov. 6, 1991

Related U.S. Application Data

[63] Continuation of Ser. No. 485,483, Feb. 27, 1990, abandoned.

[30] Foreign Application Priority Data

| Feb. 28, 1989 | [JP] | Japan | 1-47594 |
| Mar. 30, 1989 | [JP] | Japan | 1-79100 |
| Apr. 4, 1989 | [JP] | Japan | 1-85612 |
| May 12, 1989 | [JP] | Japan | 1-117372 |
| Jun. 12, 1989 | [JP] | Japan | 1-150087 |

[51] Int. Cl.$^5$ .................... C07K 15/00; A61K 45/05
[52] U.S. Cl. .................... 424/85.1; 530/351
[58] Field of Search .................... 424/85.1; 530/351

[56] References Cited

U.S. PATENT DOCUMENTS

| 4,847,325 | 6/1989 | Shadle et al. | 530/351 |
| 4,929,700 | 5/1990 | Halenbeck et al. | 530/351 |
| 4,962,091 | 10/1990 | Eppstein et al. | 424/85.1 |
| 5,021,239 | 6/1991 | Garnick | 424/85.1 |
| 5,084,556 | 1/1992 | Brown | 530/351 |

FOREIGN PATENT DOCUMENTS

| 8604607 | 8/1986 | World Int. Prop. O. |
| 8706954 | 11/1987 | World Int. Prop. O. |
| 8909060 | 10/1989 | World Int. Prop. O. |

OTHER PUBLICATIONS

Motoyoshi et al., (1986), Exp. Hematol., 14:1069–1075.
Laver et al., (Sep. 20, 1989), J. Natl. Cancer Inst., 81(18):1370–1382.
Merchav et al., (1989), Br. J. Haematology, 73:158–164.
Masaoka et al., (1988), Bone Marrow Trans., 3:121–127.
Motoyashi et al., (1986), Immunobiol., 172:205–212.
Biochemical Abstracts, vol. 87, Accession No. 89-1218162, Abstract No. 62185, "Recombinant Human Granulocyte-Macrophage Colony Stimulating Factor . . . ".
Biochemical Abstracts, vol. 87, Accession No. 89-76573, Abstract No. 40971, "Serum Cholesterol Lowering Activity of Granulocyte-Macrophage . . . ".
Garnick et al., (Apr. 1989), Clin. Res., 37(2):260A (abstract).
Shimano et al., (Aug. 5, 1990), J. Biol. Chem., 265(22):12869–12875.
Shimano et al., (May 15, 1990), Ann. N.Y. Acad. Sci., 587:362–370.
Wang et al., (1988), J. Parenteral Sci. Tech. Suppl., 42(2S):51–526.
Vadhan-Raj et al., (1987), N. Engl. J. Med., 317(25):1545–1552.
Vadhan-Raj et al., (Oct. 1989), Blood, 74(5):1491–1498.
Mufson et al., (1989), Cell. Immunol., 119:182–192.
Suzu et al., (Nov. 1, 1989), Cancer Res., 49:5913–5197.
Suzu et al., (Jan. 1990), Jpn. J. Cancer Res., 81:79–84.
Munn et al., (Aug. 1989), J. Exp. Med., 170:511–526.
Munn et al., (Jul. 1990), J. Exp. Med., 172:231–237.
Berkow, (1982), The Merck Manual of Diagnosis and Therapy, p. 2383.
White et al., (1978), Principles of Biochemistry, McGraw-Hill, N.Y., pp. 628–630, 1327–1328.
Ralph et al., (Apr. 1, 1987), Cell. Immunol., 105(2):270–279 (abstract only).
Nakoinz et al., (Oct. 15, 1988), Cell. Immunol., 116(2):331–340 (abstract only).
Sampson-Johannes et al., (Nov. 15, 1988), J. Immunol., 141(10):3680–3686.
Wing et al., (1982), J. Clin. Invest., 69:270–276.
Li et al., (Mar. 1989), J. Exp. Med., 169:973–986.
Motoyoshi et al., (1989), Lancet, vol. II, (No. 8658):326–327.
Stoudemire et al., (Feb. 15, 1991), Blood, 77(4):750–755.
Dexter et al., (1984), Nature, 309:746–747.
Andreeff et al., (Jun. 1989), Sem Oncol., 16(3):211–229.
Nadler, (1990), Cancer Invest., 8(2):299–300.
Wang et al., (1983), J. Cell. Biochem., 21:263–275.

*Primary Examiner*—Robert A. Wax
*Assistant Examiner*—Keith D. Hendricks
*Attorney, Agent, or Firm*—Oblon, Spivak, McClelland, Maier & Neustadt

[57] ABSTRACT

Human M-CSF preparations and recombinant human M-CSF preparations against myelodysplastic syndrome, malignant tumor and hyperlipemia and auxiliary therapeutic preparations to be dosed along with platinum-complex anticancer preparations.

8 Claims, 9 Drawing Sheets

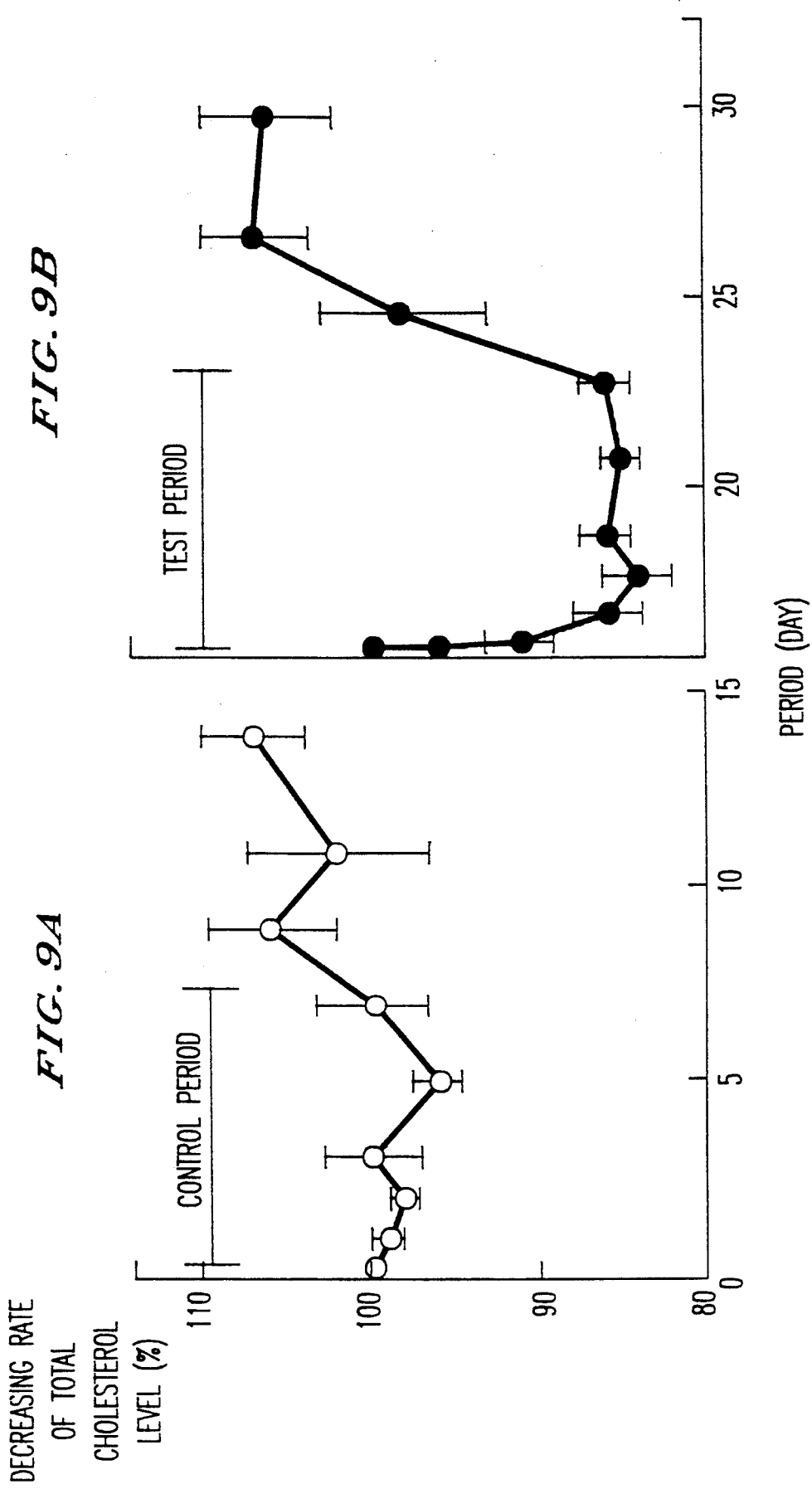

HUMAN MONOCYTE-MACROPHAGE-CSF PREPARATIONS

This application is a continuation of application Ser. No. 07/485,483, filed on Feb. 27, 1990, now abandoned.

FIELD OF THE INVENTION

The present invention relates to human monocyte-macrophage colony stimulating factor (hereinafter abbreviated as hM-CSF) preparations.

More particularly, the present invention relates to therapeutic preparations containing hM-CSF as the effective component on Myelodyslastic syndrome (hereinafter abbreviated as MDS).

The present invention relates to therapeutic preparations containing hM-CSF, particularly originating from human urine, as the effective component against malignant tumor.

The present invention also relate to auxiliary therapeutic preparations containing hM-CSF to be dosed on therapy with platinum complex preparations against malignant tumors.

The present invention also relates to a therapeutic preparation containing hM-CSF as an effective component against hyperlipemia.

The present invention relates to a therapeutic preparation containing recombinant hM-CSF (hereinafter abbreviated as rhM-CSF) as an effective component against hyperlipemia.

BACKGROUND OF THE INVENTION

Colony stimulating factors (hereinafter abbreviated as CSFs) are known as substances which stimulate proliferation and differentiation of hematopoietic stem cells, and they are categolized into following four items:
(1) factors which act on monocyte-macrophage lineage (M-CSFs),
(2) factors which act on granulocyte-monocyte lineage (GM-CSFs),
(3) factors which act on granulocyte lineage (G-CSFs), and
(4) factors which act on multipotential stem cells (multi-CSFs)

Human M-CSFs are already isolated and purified, and their protein structures and genetic structure which participates production of M-CSFs or which encode amino acid sequence of M-CSFs have been described (cf: Japanese Unexamined Patent Application Gazette No. 64(1989)/22899).

Regarding tumoricidal activity of a CSF is described by A. Samson-Johannes et al (cf: Journal of Immunology, Vol. 141, 3680–3686, No. 10, Nov. 15, 1988).

It is also described that an hM-CSF may stimulate matured human monocyte-macrophage to produce various cytokines (cf: K. Motoyoshi et al, Experimental Hematology, Vol. 17, 68–71, 1989), that a human urinary M-CSF is clinically effective on granulocytopenia (cf: K. Motoyoshi et al, Experimental Hematology, Vol. 14, 1069–1075, 1986), and that a human urinary M-CSF is clinically effective in recovery of leukocyte and granulocyte numbers after bone marrow transplantation (cf: T. Masaoka et al, Bone Marrow Transplantation, Vol. 3, 121–127, 1988). Therefore, human M-CSFs have been highly expected to be used as a drug.

With respect to the safeness and scarce side effects in dosage of hM-CSFs have been clinically confirmed (cf: K. Motoyoshi et al, Immunobiology, Vol. 172, 205–212, 1986).

It has been known that monocyte-macrophage lineage is significantly related with hyperlipemia and arteriosclerosis.

PROBLEMS IN THE PRIOR ART

MDS (Myelodysplastic Sndrome) is a name assigned to aggregation of symptoms wherein quantitative and qualitative disorders are found in one or more of hematopoietic system comprising erythrocytes, granulocytemonocytes, and platelets lineages. In this syndrome, various disorders are typically found widely in the bone marrow and the peripheral blood, for example, macrocytepemia, ringedsideroblastic anemia, megaloblastic anemia, neutropenia and thrombocytopenia, and chromosome aberration.

MDS are categorized into 5 types depending upon patients' conditions or conditions of diseases; refractory anemia (RA), RA with ringed sideroblastosis, RA with excess blasts (RAEB), chronic myelomonocytic leukemia (CMML), and RAEB in transformation. Although the symptoms are greatly different depending upon the types, any types of MDS are ultimately inverted into myelogeneous leukemia, which is a mortal disease, after elapse of few months or few years. Although minimum Ara-C dosing therapy or $VD_3$ therapy have been clinically applied, therapeutic results are not satisfactory. Therefore, establishment of an effective therapy has been earnestly desired.

However, it has been remained to be studied regarding utilizability of hM-CSF against MDS.

Therapeutic effects against malignant tumors have been improved by developments of chemotherapeutic preparations as well as improvements in surgical techniques. Complete elimination of malignant tumors, however, has not been achieved, and relapses have been often observed. It is also the problem that chemotherapeutic preparations have severe side effects on the various organs, and that dosage of chemotherapeutic preparations have often caused heavy infectious diseases and/or organopathy. Consequently, bone marrow transplantation after heavy or strong chemotherapy has been tried for radical cure. In bone marrow transplantation, bone marrow grafts from donors having coincident or matching HLA type have been utilized, however, manifestation of grafts-versus-host ractions (GVHR) have been often observed. Therefore, homologous bone marrow transplantation is desirable. In the case of tumors on hematopoietic organs, inclusion of malignant tumor cells in bone marrow cells to be transplanted (or in the grafts) is inevitable, thus purge of malignant tumor cells has been essential.

However, it has been remained to be studied regarding utilizability of human urinary M-CSF against malignant tumors.

Medical treatments against malignant tumors also include surgical treatment, chemotherapy and radiotherapy. Therapeutic effects against malignant tumors have been improved by developments of chemotherapeutic preparations as well as improvements in surgical techniques. However, there is no chemotherapeutic preparation which has remarkable therapeutic efficacies but less side effects, thus there were upper limits of their dosages. Again, complete elimination of malignant tumors has not been achieved, and relapses have been often observed. There are chemotherapeutic preparations which show serious toxicities against hematopoietic organs and various other organs resulting in organic troubles and/or heavy infectious diseases. For example, anticancer preparations containing platinum complex compound have excellent anti-tumor activities (cf: B. Rosenberg et al, Nature, 205, 698, 1965). It has been reported that cis-platinum diamine dichloride (cisplatin, CDDP), which is one of platinum complex preparations, has a strong anti-tumor activity and that it demonstrated a remarkable effect against malignant ureteral tumors and gynecological malignant tumors which had hitherto been difficult to cure by chemotherapy (cf: Merrin C. E., Cancer Treat. Rep., 63,1579, 1979). It was a problem that these chemotherapeutic preparations have strong toxicity on kidneys and hematopoietic organs, and often result in renal insufficiency, thrombocytopenia, anemia and other serious side effects.

It has been also remained to be studied regarding utilizability of hM-CSF as auxiliary preparation against side effects caused by anticancer chemotherapy, especially by platinum complex preparations.

Hyperlipemia is known as a disease wherein serum levels of one or more of cholesterol, neutral fats, and phospholipids are increased over the respective normal or reference values. The reference values for hyperlipemia for Japanese are settled as 200 mg of total cholesterol, 130 mg of neutral fats, and 250 mg of phospholipids per 100 ml of blood respectively. Hyperlipemia by itself is not serious disease, however, when it is left as it is, it may result in arteriosclerosis, and it may be an inducement for angina pectoria or stenocardia and myocardial infarction, thus it may result in a serious consequences in clinical view point. Although there are many drugs against hyperlipemia and arteriosclerosis, clinically probucol (cf: A. Watanabe et al, Arteriosclerosis in Japanese, Vol. 11, No. 3, 597, 1983) and elastase (cf: S. Yoshimura, Arteriosclerosis in Japanese, Vol. 3, 223, 1975) have been mainly utilized. The functions of these drugs are to minimise adherence of cholesterol to vascular walls or washing out cholesterol therefrom, however, there are limitations of their effects and there is no drug to achieve radical cure of hyperlipemia.

However, it has been remained to be studied regarding utilizability of hM-CSF against hyperlipemia and arteriosclerosis.

It has been also remained to be studied regarding utilizability of rhM-CSF against hyperlipemia and arteriosclerosis.

SOLUTION OF THE PROBLEMS

Some of the inventors (F. Takaku and K. Motoyoshi) of the present application conducted studies about utilizability of hM-CSF as a therapeutic preparation against MDS. As the results, it has been found that recovery from decrease or disappearance of myeroblast cells which are serious problems resulted from MDS, and increase in normal leukocyte and normal erythrocyte counts can be achieved by dosage of hM-CSF. The present invention is based on the discovery.

Some of the inventors (T. Kawashima, N. Yanai, M. Yamada, H. Yokota, K. Ujiie, K. Yoshida and S. Suzu) of the present application have conducted studies about utilization of hM-CSF to kill and wound malignant tumor cells, and found that hM-CSF may augment the tumoricidal activity of macrophage. The present invention is based on the discovery.

Some of the inventors (T. Kawashima, N. Yanai, M. Yamada, H. Yokota and K. Yoshida) of the present application have conducted studies about drugs which may restrain or reduce the side effects of CDDP which has a highly antitumor activity. As the results they found that hM-CSF may largely reduce or minimize troubles on kidneies and hematopoitetic organs caused by platinum-complex preparations for malignant tumors and that it may lower mortality rate caused by acute toxicity of the platinum-complex preparations. The present invention is based on this discovery.

Some of the inventors (F. Takaku, K. Motoyoshi and N. Yamada) of the present application have conducted studies about utilization of hM-CSF against hyperlipemia and arteriosclerosis with respect to patients suffering from hyperlipemia and model animals of hyperlipemia. As the results they found that hM-CSF has a function for lowering the blood cholesterol level and the blood neutral fats level which are the most important factors in hyperlipemia and arteriosclerosis. The present invention is based on this discovery.

Some of the inventors (F. Takaku and K. Motoyoshi) of the present application have conducted studies about utilization of rhM-CSF against hyperlipemia and arteriosclerosis. As the results they found that rhM-CSF has a function for lowering the serum cholesterol level and the serum neutral fats level which are the most important factors in hyperlipemia and arteriosclerosis. The present invention is based on this discovery.

OBJECTS OF THE INVENTION

Therefore, it is an object of the present invention to provide hM-CSF preparations.

It is a particular object of the present invention to provide therapeutic preparation containing hM-CSF as an effective component against MDS.

It is a further object of the present invention to provide an anticancer preparation containing human urinary M-CSF as an effective component which has remarkable anti-cancer activity and which has no severe side effect.

It is a still further object of the present invention to provide a regimen wherein the anticancer preparation containing hM-CSF as an effective component is dosed together with specific antibody to malignant tumors.

It is a further object of the present invention to provide an auxiliary preparation containing hM-CSF as an effective component which is dosed together with anticancer preparation containing platinum complex compounds.

It is a still further object of the present invention to provide an auxiliary preparation containing hM-CSF as an effective component for reducing or minimising side effects caused by the platinum complex compound preparations.

It is an object of the present invention to provide auxiliary preparation containing hM-CSF as an effective component to be dosed together with the platinum complex preparations for reducing troubles on kidneis and/or hematopoietic organs caused by the latter.

It is also an object of the present invention to provide a therapeutic preparation containing hM-CSF as an effective component against hyperlipemia and arteriosclerosis.

It is a further object of the present invention to provide a therapeutic preparation containing rhM-CSF as an effective component, which is produced by mammalian cells transfected with the hM-CSF producing gene, against hyperlipemia and arteriosclerosis.

Human M-CSF used in the present invention may be those prepared from human urine or culture broth in which hM-CSF producing cells or mammalian cells transfected with the hM-CSF producing gene are cultivated.

It is also an object of the present invention to provide hM-CSF preparations in which surface active agents and/or proteins such as Tween 80, human serum albumine or gelatine are contained as stabilizing agents for hM-CSF. Although, effectiveness of other stibilizers other than those specifically enumaerated have not yet been confirmed, it is apparently anticipated that other surface active agents and other proteins originating from humanbeings will be effective.

DETAILED DESCRIPTION OF THE INVENTION

Figure 1:
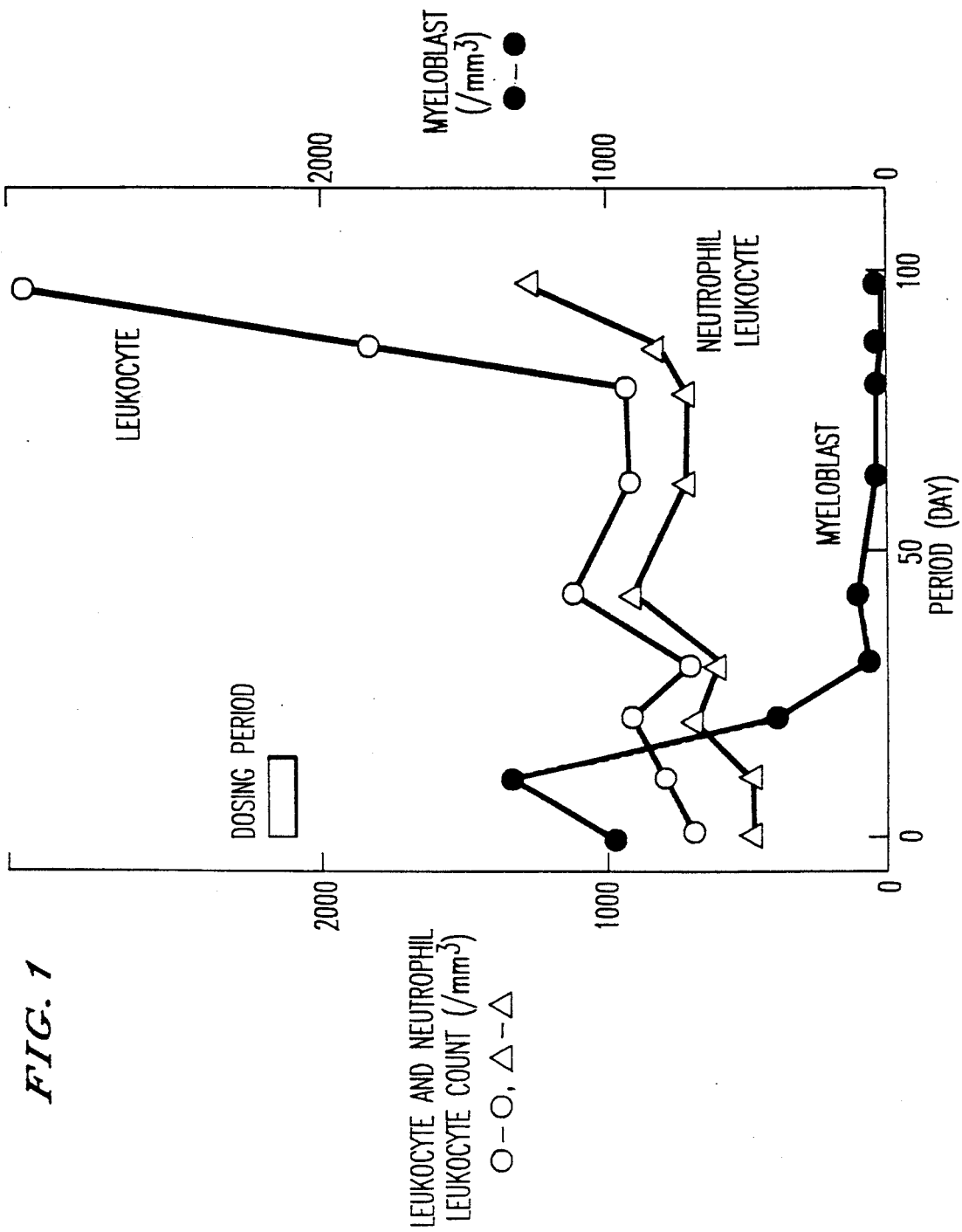

Human urinary M-CSF and rhM-CSF used in the present invention as hM-CSF was isolated, purified and freeze-dried in accordance with the known procedures described hereinafter.

Following references are incorporated herein as the records of prior art for preparation of hM-CSF.

Japanese Unexamoned Patent Application Gazette No. 63(1988)-198700,

Japanese Unexamined Patent Application Gazette No. 63(1988)-250400,

Japanese Unexamined Patent Application Gazette No. 64(1989)-22899

U.S. patent application No. 860377, and

U.S. patent application No. 940362

PREPARATION OF HUMAN URINARY M-CSF, #1 cf: Japanese Unexamined Patent Application Gazette No. 63(0988)/198700

From healthy men, 1,000 l of human urine was collected, and its pH was adjusted to 8.5 to remove precipitate with a filter. The resultant filtrate was concentrated and demineralized using ultrafiltration membranes (by Amicon, H 10×50). Resultant concentrate was adjusted its pH to 7.0, then pasturized in an air-tight container at 60° C. for 10 hours. The pasturized liquid is centrifuged (5,000 G×30 min.) to remove precipitates, then resultant supernatant was treated with DEAE-cellurose culumn, which had been preliminarily equilibrated with 0.02M phosphate buffer solution (pH 7.2), for adsorption. After washing the DEAE-cellurose with 0.02M phosphate buffer solution (pH 7.2) containing 0.05M sodium chloride, elution was carried out using 0.02M phosphate buffer solution (pH 7.2) containing 0.25M sodium chloride. The resultant eluate was concentrated with an ultrafiltration membrane (by Amicon, H 10 P 10), thus obtained concentrate was subjected to gel filtration by Sephacryl S-30 (trademark, by Pharmacia, 20 cm diameter×80 cm hight) with buffer solution (pH 7.2) containing 1M ammonium sulfate. The 70,000−50,000 daltons fraction obtained from the gel filtration was applied to phenyl-Sephalose 4B column (trademark, by Pharmacia, 10 cm diameter×20 cm hight), which had been preliminarily equilibrated with the buffer solution containing ammonium sulfate, for adsorption, then eluted with the same buffer solution (pH 7.2) containing 0.5M ammonium sulfate. The resultant eluate was concentrated with an ultrafiltration membrane (by Amicon, H 1 P 10). The resultant concentrate was subjected to liquid chromatography (TSK-G3000SW, by Toso, 2 cm diameter×60 cm hight) thereby obtained the fraction of relative eluate quantity (Ve/Vo) 1.2-1.5. The resultant fraction was concentrated again, thus obtained concentrate was subjected to reversed-phase high performance liquid chromatography (hereinafter abbreviated as RP-HPLC) using Hi-Pore 214 Tp column (by Biduck, 2.2 cm×25 cm hight) with 0–100% linear concentration gradient of acetonitrile containing 0.1% trifluoroacetic acid, thereby hM-CSF fraction was collected. The collected hM-CSF fraction was freeze-dried, 4 mg of human urinary M-CSF was obtained.

PREPARATION OF HUMAN M-CSF, #2 cf: Japanese Unexamined Patent Application Gazette No. 64(1989)/22899

Anti-hM-CSF antibody, which was collected from rabbits immunized with purified hM-CSF, was dyalized against 0.1M phosphate buffer solution (pH 7.0) to obtain 20 mg/ml antibody solution. To 100 g of Formyl-Cellulofine (trademark, by Chisso Manuf.), which had been previously washed with distilled water and 0.1M phosphate buffer solution, 200 ml of the antibody solution was added, and the resultant mixture was stirred at room temperature for adsorption, then 700 mg of sodium cyanoboron hydride was further added and stirred for 16 hours to thereby obtain antibody-bonded carriers wherein anti-hM-CSF antibody was bonded to Formyl-Cellulofine (trademark, Chisso Manuf.). The resultant antibody-bonded carrier was washed with 0.2M tris-HCl buffer solution, then 200 ml of the tris buffer solution containing 500 mg of sodium cyanoboron hydride was added and stirred for 4 hours at room temperature to deactivate unreacted formyl groups. The resultant antibody-bonding carrier was sufficiently washed with 0.02M phosphate buffer solution containing 0.5M NaCl. The washed antibody-bonding carrier contained 29.5 mg of anti-hM-CSF antibody per g of the antibody-bonded carrier.

Human urine concentrate, which was prepared from 1000 l of human urine by concentration and dimineralization with an ultrafiltration concentrator, was adsorped to DEAE-cellurose to remove unadsorbed contaminants, then eluted with 0.3M NaCl solution. To the eluate, NaCl was added to prepare solution containing hM-CSF and 0.5M NaCl. Specific activity of the resulted hM-CSF solution was $2 \times 10^5$ U/mg.

To 100 g of the previously prepared antibody-bonded carrier, the previously prepared hM-CSF solution was added to make 500 ml of the mixture in total quantity, the resultant mixture was stirred at a temperature equal to or lower than 10° C. over one night, then subjected to batchwise chromatography. The antibody-bonded carrier capturing hM-CSF was collected by filtration through a glass filter under aspiration and washed with 0.02M phosphate buffer solution containing 0.5M NaCl for three times. To the washed antibody-bonded carrier, 500 ml of 0.2M acetate buffer solution (pH 2.5) was added, then stirred at 10° C. for 1 hour to elute hM-CSF. The resulted eluate was adjusted its pH to 7.0, then concentrated and dimineralized by an ultrafiltration membrane to thereby obtain hM-CSF fraction. The resultant fraction was subjected to RP-HPLC using Hi-Pour 214 Tp (by Biduck, 2.2 cm diameter×25 cm hight) with 0–100% linear-dencity gradient of acetonitrile containing 0.1% trifluoroacetic acid to collect purified hM-CSF solution. The resulted solution was freeze-dried to obtain 3.2 mg purified hM-CSF. The specific activity of the purified hM-CSF was $1.4 \times 10^4$ U/mg, and its purity was >96% by SDS-PAGE method.

PREPARATION OF HUMAN M-CSF, #3 cf: Japanese Unexamined Patent Application Gazette No. 63(1988)-250400

Anti-hM-CSF antibody, which was obtained from rabbits immunized with purified hM-CSF, was dyalized against 0.1M phosphate buffer solution (pH 7.0) to thereby obtain a solution containing the antibody in the concentration of 20 mg/ml. To 100 g of Formyl Cellulofine (trademark, by Chisso Manuf.), which had been previously washed with distilled water and 0.1M phosphate buffer solution, 200 ml of the antibody solution was added and stirred for 2 hours at room temperature for adsorption then 700 mg of sodium cyanoboron hydride was further added thereto and stirred for 16 hours to prepare antibody-bonded carrier. The resultant antibody-bonded carrier was washed with 0.2M tris-HCl buffer solution, then 200 ml of the tris buffer solution containing 500 mg of sodium cyanoboron hydride was further added and stirred for 4 hours at room temperature to deactivate unreacted formyl groups. The resulted antibody-bonded carrier was sufficiently washed with 0.02M phosphate buffer solution containing 0.5M NaCl. The washed antibody-bonded carrier contained 29.5 mg of anti-hM-CSF antibody per g antibody-bonded carrier.

Human urine concentrate, which was prepared from 1000 ml of human urine by concentration and dimineralization with an ultrafiltaration concentrator, was introduced into DEAE-cellurose column to remove unadsorbable contaminants, then eluted with 0.3M NaCl solution. To the resultant eluate, NaCl was added to prepare a solution containing hM-CSF and 0.5M NaCl. The specific activity of the hM-CSF solution was $2 \times 10^5$ U/mg.

to 100 g of the previously prepared antibody-bonded carrier, the previously prepared hM-CSF solution was added to obtain 500 ml of the mixture in total quantity, the resultant mixture was stirred at a temperature equal to or lower than 10° C. over one night, then subjected to batchwise chromatography. The antibody-bonded carrier capturing hM-CSF was collected by filtration through a glass filter under aspiration and washed with 0.02M phophate buffer solution containg 0.5M NaCl for three times. To the washed carrier, 500 ml of 0.2M acetate buffer solution (pH 2.5) was added, then stirred at 10° C. for 1 hour to elute hM-CSF. After adjusting pH of the resultant eluate to pH 7.0, it was subjected to concentration and dimineralization by an ultrafiltration membrane to thereby obtain 10 mg of purified hM-CSF. The specific activity of the purified hM-CSF was $5.2 \times 10^7$ U/mg, and the purity was >90% by SDS-PAG method.

PREPARATION OF rhM-CSF

Antibody-bonded carrier of rhM-CSF was prepared, washed, and then deactivated the unreacted formyl groups in the same manner as in [PREPARATION OF HUMAN M-CSF, #2]. The resulted antibody-bonded carrier was fully washed with 0.02M phosphate buffer solution containing 0.5M NaCl. The washed carrier contained 32.6 mg of anti-rhM-CSF antibody per g thereof.

Ten l of a culture broth, which was resulted by incubation of mammalian cells transfected with the hM-CSF producing gene (CHO cells) in a culture medium, was conentrated and demineralized by an ultrafiltration concentrator to thereby obtain its concentrate. The resulted concentrate was adsorbed to DEAE-cellurose column to remove unadsorbed contaminants, then subjected to elution with 0.3M NaCl solution. To the eluate, NaCl was added to obtain hM-CSF solution containing 0.5M NaCl. The specific activity of the resultant hM-CSF solution was $3 \times 10^6$ U/mg.

To 100 g of the previously prepared anibody-bonded carrier, said hM-CSF solution was added to obtain 500 ml of the mixture in total quantity, the resulted mixture was stirred at a temperature equal to or lower than 10° C. over one night, then subjected to batchwise chromatography. The antibody-bonded carrier capturing rhM-CSF was collected by filtration through a glass filter under aspiration and washed with 0.02M phosphate buffer solution containing 0.5M NaCl for three times. To the washed antibody-bonded carrier capturing rhM-CSF, 500 ml of 0.2M acetate buffer solution (pH 2.5) was added and stirred at 10° C. for 1 hour to elute rhM-CSF. The resultant eluate was adjusted its pH to 7.0, then concentrated and dimineralized by ultrafiltration membrane to thereby obtain rhM-CSF fraction. This fraction was subjected to RP-HPLC using Hi-Pour 214TP column (by Biduck, 2.2 cm diameter×25 cm hight) with 0-100% linear-concentration gradient of acetonitrile (pH 2.0) containing 0.1 trifluoroacetic acid, to thereby obtain purified rhM-CSF solution. The purified solution was freeze-dried to obtain 25 mg of purified rhM-CSF. The specific activity of the resultant rhM-CSF was $1.9 \times 10^8$ U/mg, and its purity was >98% by SDS-PAGE method.

Physico-chemical natures of the hM-CSF obtained by any of the forgoing methods were as follows:

a) MOLECULAR WEIGHT

The obtained hM-CSF was a homo-dimer consisting of equivalent or homologous subunits and its molecular weight is 70,000–90,000 daltons measured by sodium dodecylsulfate polyaclylamide gel electrophoresis. The molecular weight of the subunit which was obtained by dissociation of the dimar with reducing agents to diactivate its biological activity was 35,000–45,000 daltons measured by the same method.

b) AMINO ACID SEQUENCE OF THE SUBUNIT PROTEIN OF hM-CSF

The subunit protein of the homodimar of hM-CSF isolated from human urine hasd 214–238 amino acid sequence shown hereunder and the asparagin located at 122nd and 140th had typical N-glycoside bondings represented by "asparagine (Asn)-x-threonine (Thr)/serine (Ser)", wherein x denotes an optional amino acid. Just for reference, subunit protein of the homodimar of rhM-CSF has 223 amino acid sequence as shown hereunder.

```
1
Glu—Glu—Val—Ser—Glu—Tyr—Cys—Ser—His—Met—
Ile—Gly—Ser—Gly—His—Leu—Gln—Ser—Leu—Gln—
Arg—Leu—Ile—Asp—Ser—Gln—Met—Glu—Thr—Ser—
Cys—Gln—Ile—Thr—Phe—Glu—Phe—Val—Asp—Gln—
Glu—Gln—Leu—Lys—Asp—Pro—Val—Cys—Tyr—Leu—
Lys—Lys—Ala—Phe—Leu—Leu—Val—Gln—Asp—Ile—
Met—Glu—Asp—Thr—Met—Arg—Phe—Arg—Asp—Asn—
Thr—Pro—Asn—Ala—Ile—Ala—Ile—Val—Gln—Leu—
Gln—Glu—Leu—Ser—Leu—Arg—Leu—Lys—Ser—Cys—
Phe—Thr—Lys—Asp—Tyr—Glu—Glu—His—Asp—Lys—
Ala—Cys—Val—Arg—Thr—Phe—Tyr—Glu—Thr—Pro—
```

-continued

Leu—Gln—Leu—Leu—Glu—Lys—Val—Lys—Asn—Val—

122
Phe—Asn—Glu—Thr—Lys—Asn—Leu—Leu—Asp—Lys—

140
Asp—Trp—Asn—Ile—Phe—Ser—Lys—Asn—Cys—Asn—

Asn—Ser—Phe—Ala—Glu—Cys—Ser—Ser—Gln—Asp—
Val—Val—Thr—Lys—Pro—Asp—Cys—Asn—Cys—Leu—
Tyr—Pro—Lys—Ala—Ile—Pro—Ser—Ser—Asp—Pro—
Ala—Ser—Val—Ser—Pro—His—Gln—Pro—Leu—Ala—
Pro—Ser—Met—Ala—Pro—Val—Ala—Gly—Leu—Thr—
Trp—Glu—Asp—Ser—Glu—Gly—Thr—Glu—Gly—Ser—
Ser—Leu—Leu—Pro—Gly—Glu—Gln—Pro—Leu—His—

214
Thr—Val—Asp—Pro—Gly—Ser—Ala—Lys—Gln—Arg—

223
Pro—Pro—Arg—Ser—Thr—Cys—Gln—Ser—Phe—Glu—

238
Pro—Pro—Glu—Thr—Pro—Val—Val—Lys— c) ISOELECTRIC POINT

The isoelectric point (pI) of the homo dimar measured by isoelectric point electrophoresis of polyacrylylamide gel and by suclose-density-gradient isoelectric point electrophoresis fell within the range of 3.1–3.7.

d) CIRCULAR DICHROISM SPECTRUM

Minimum peaks at 208 and 222 nm (wave length) were observed in far-ultraviolet ray CD spectrum of the homodimar measured by a circular dichroism polarimeter, and it was suggested to have an α-helix structure.

e) THERMAL STABILITY

The homodimar did not lose its biological activity when heated at 60°±0.5° C. for 60 minutes.

f) INFRARED ABSORPTION SPECTRUM

Intense absorption was observed at 1680 cm$^{-1}$ and 1130 cm$^{-1}$ (wave length) and medium intense absorption was observed at 1540 cm$^{-1}$, 1430 cm$^{-1}$ and 1070 cm$^{-1}$ in infrared absorption spectrum.

The hM-CSF prepared in accordance with the foregoing methods can be parenterally dosed (for example, intravenously, arteryally, intramascularlly, subcutaneously and intraabdominally). Injections and infusions containing hM-CSF in accordance with the present invention can be prepared by any conventional methods. For example, hM-CSF prepared in accordance with the present invention can be added to a preferable buffer solution, the resultant solution can be subjected to sterile membrane filtration, the resultant filtrate can be aseptically filled in vials then sealed to provide such products for injections and infusions. If required, the filtrate can be freezedried.

It should be noted, however, that hM-CSF has a property to adhere onto surfaces of glass, plastics and sterile membrane filters. This adhesivness can be eliminated by adding such additives, for example, surface active agents, human serum albumin and/or gelatin, It has been found that inclusion of surface active agents and/or proteins such as Tween 80, human serum albumin and gelatine may remarkably improve the biological activities of hM-CSF. Preferable concentrations of the additives are: more than 0.2 μg/ml for surface active agents; more than 1 mg/ml of hM-CSF preparation, or 100 fold weight part of human serum albumine or gelatin to hM-CSF.

Figure 2:
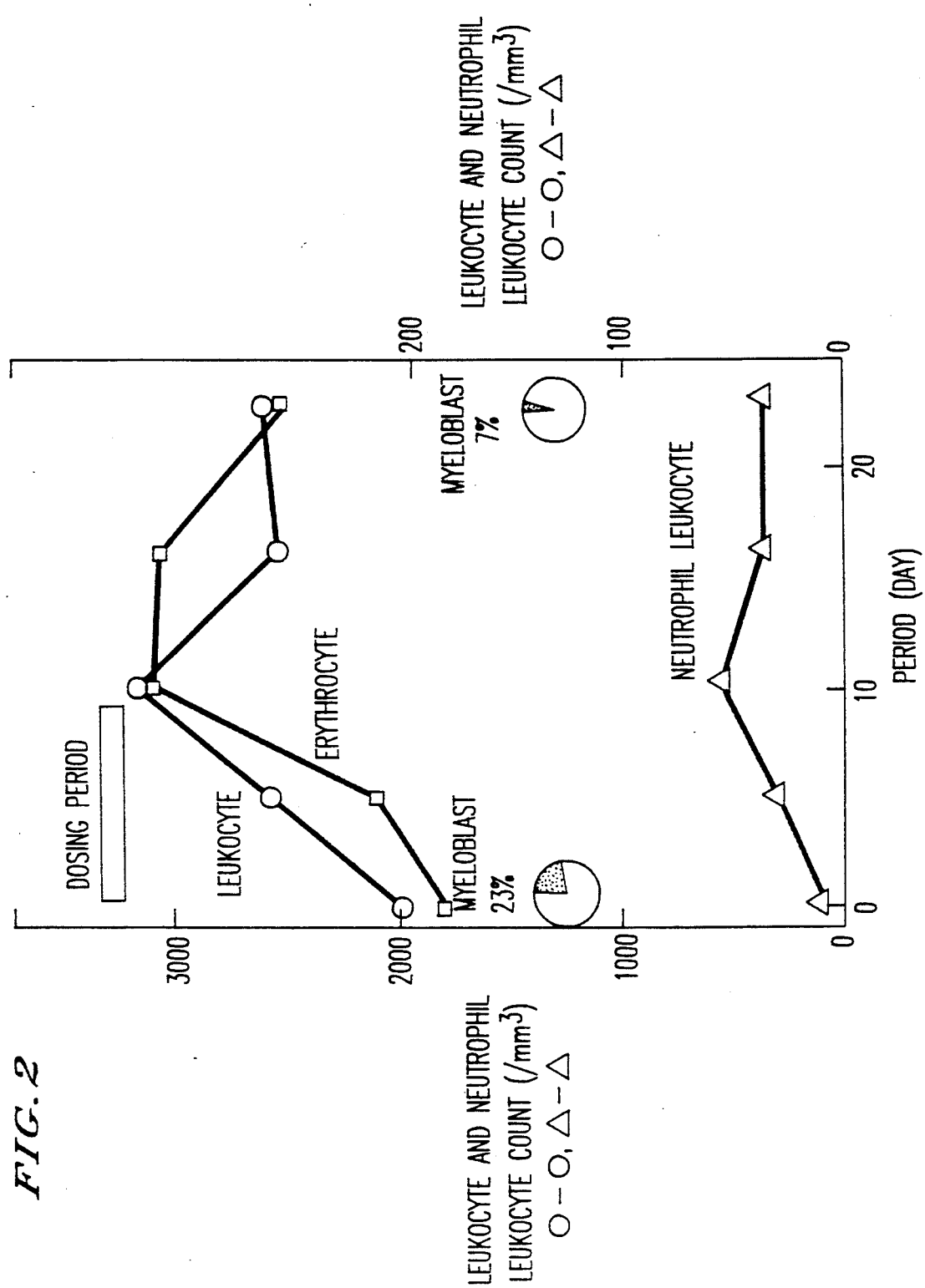
Figure 3:
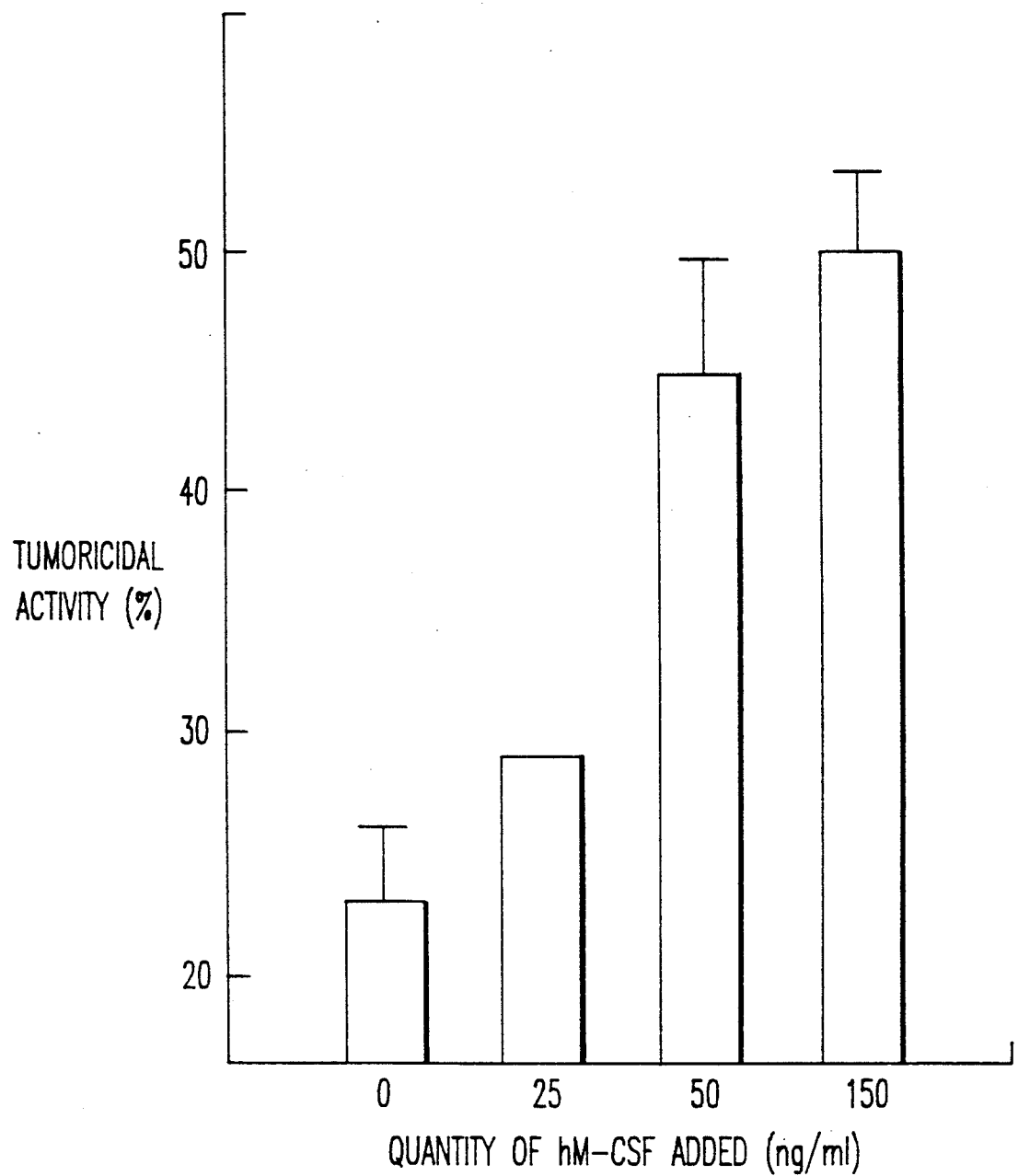
Figure 4:
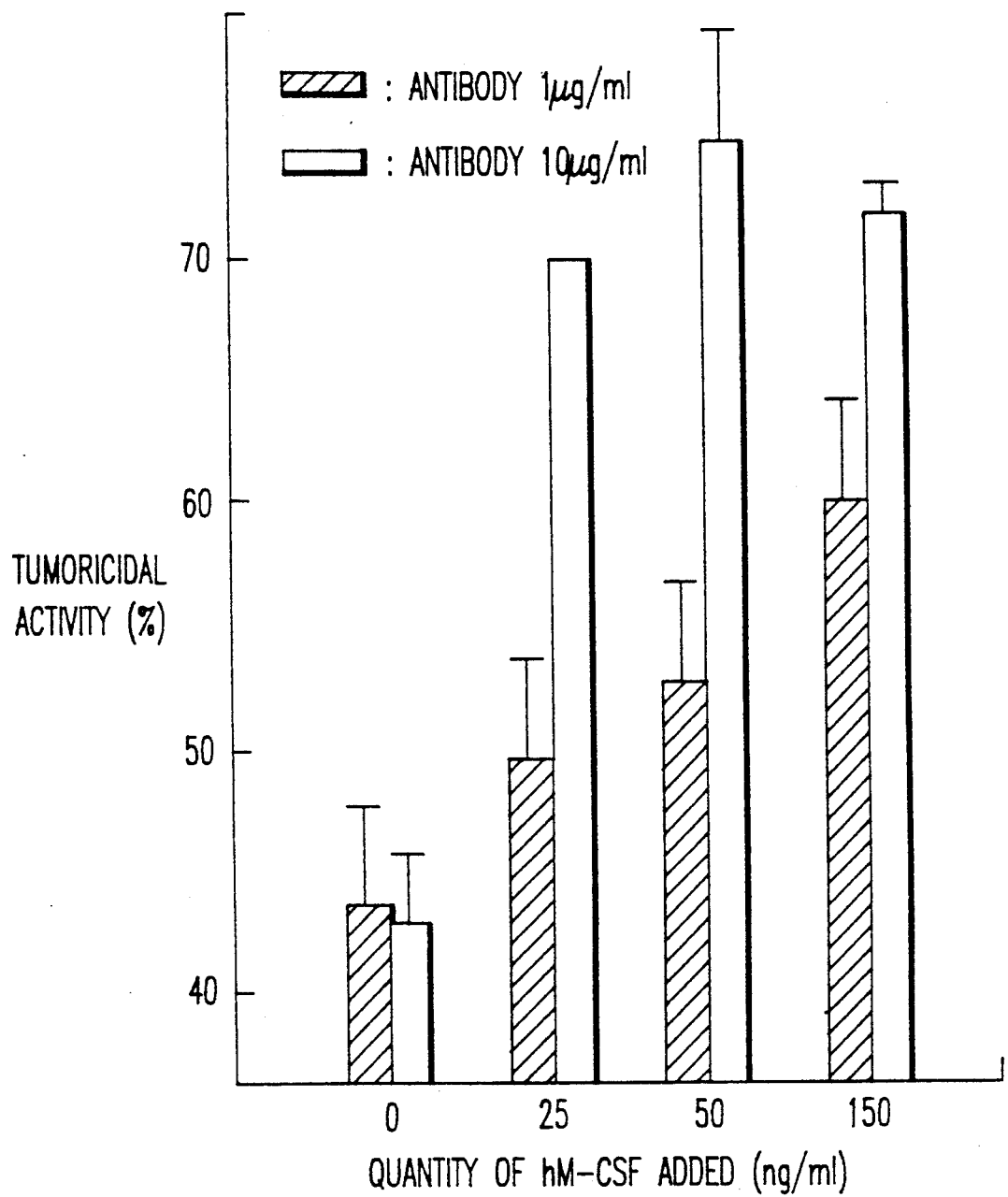
Figure 5:
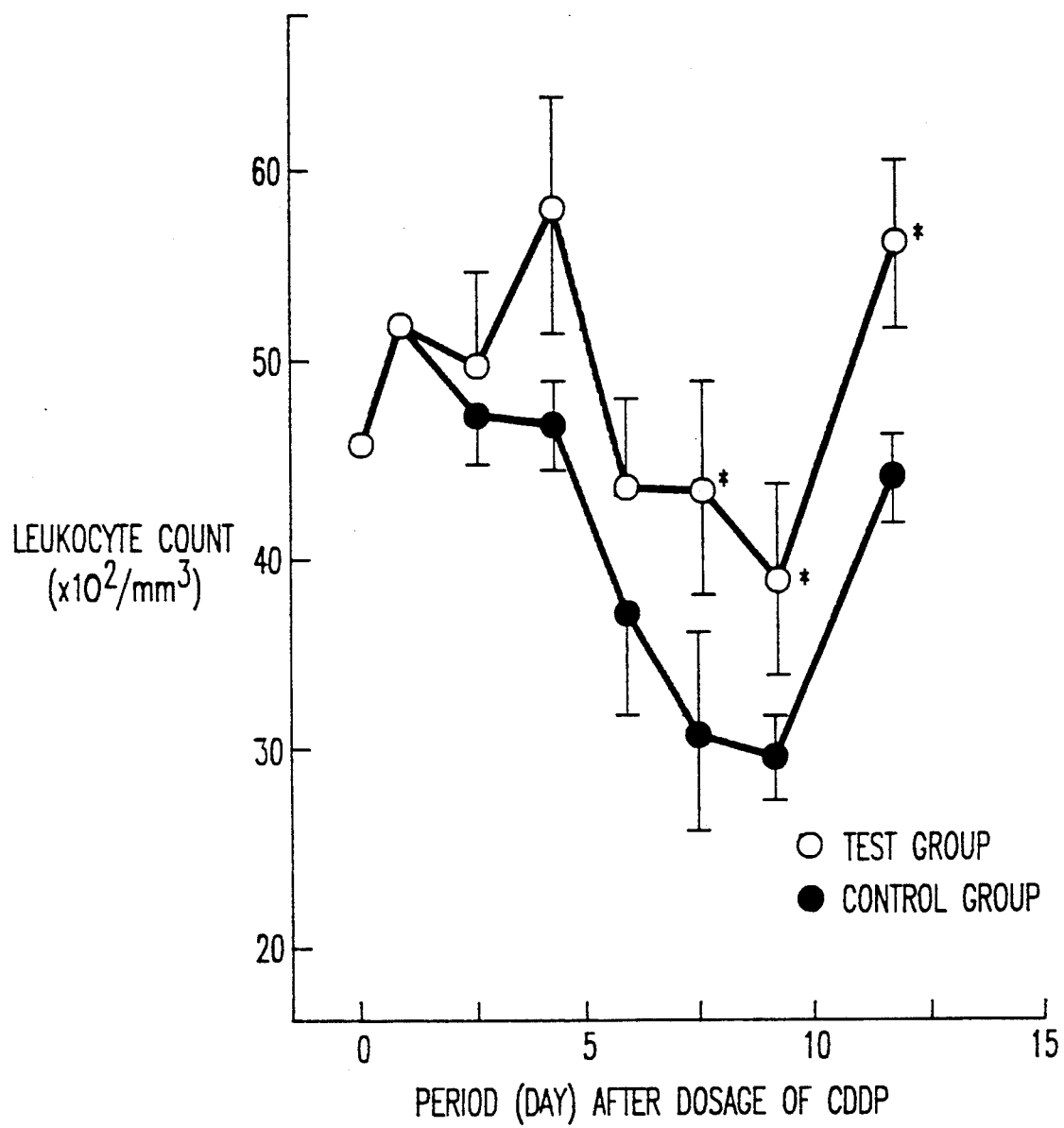
Figure 6:
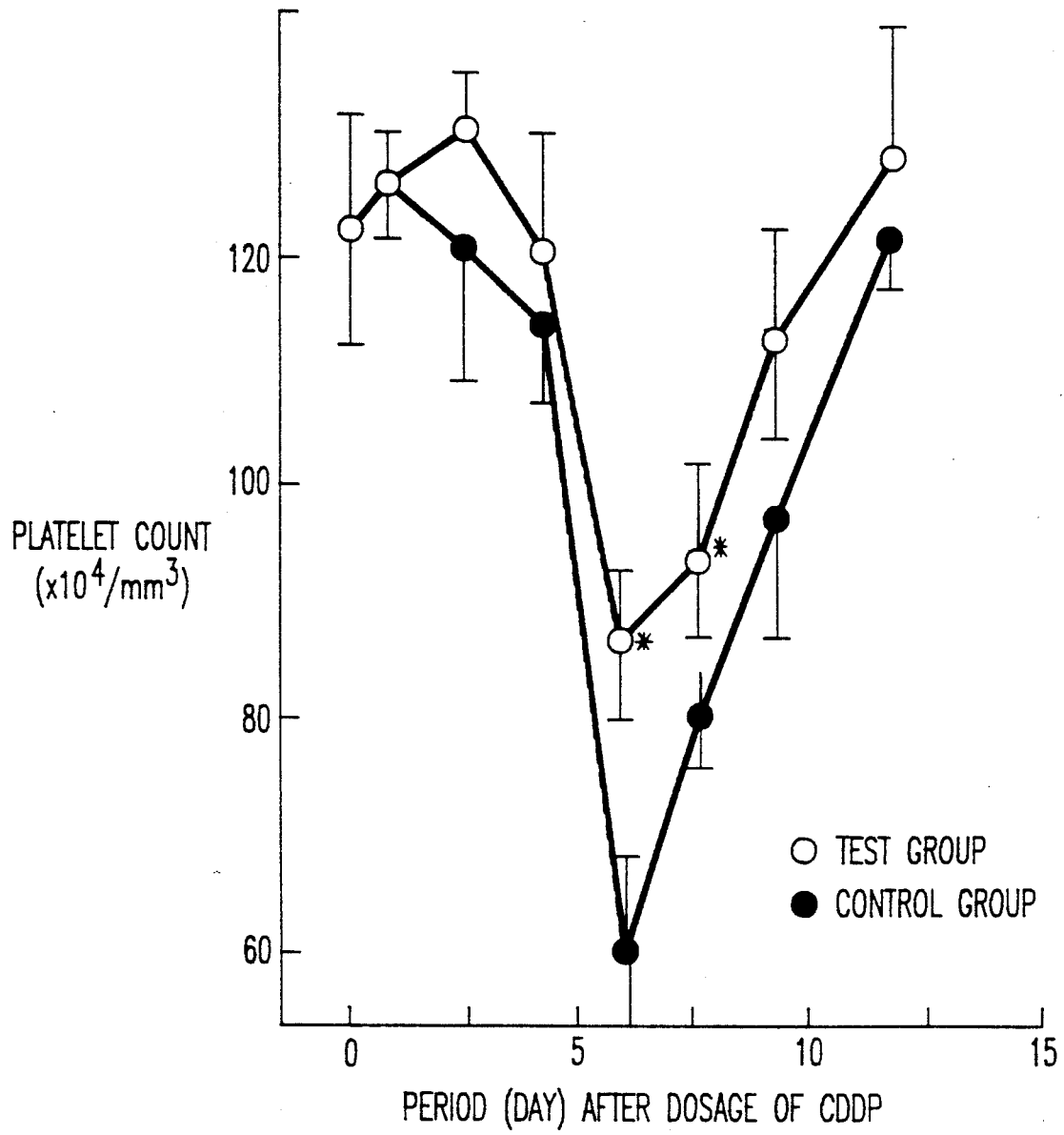
Figure 8:
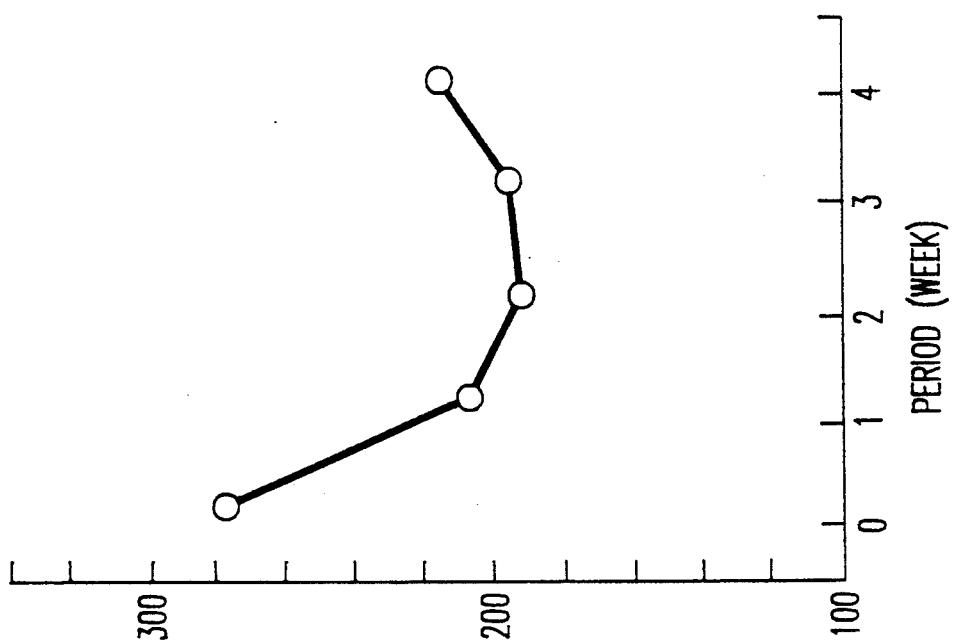
Figure 7:
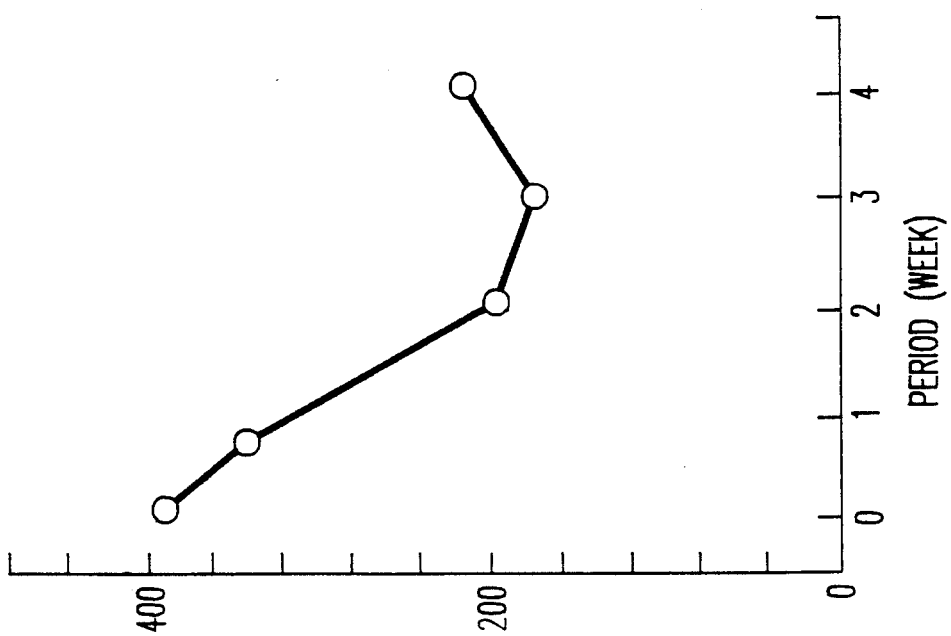
Figure 10:
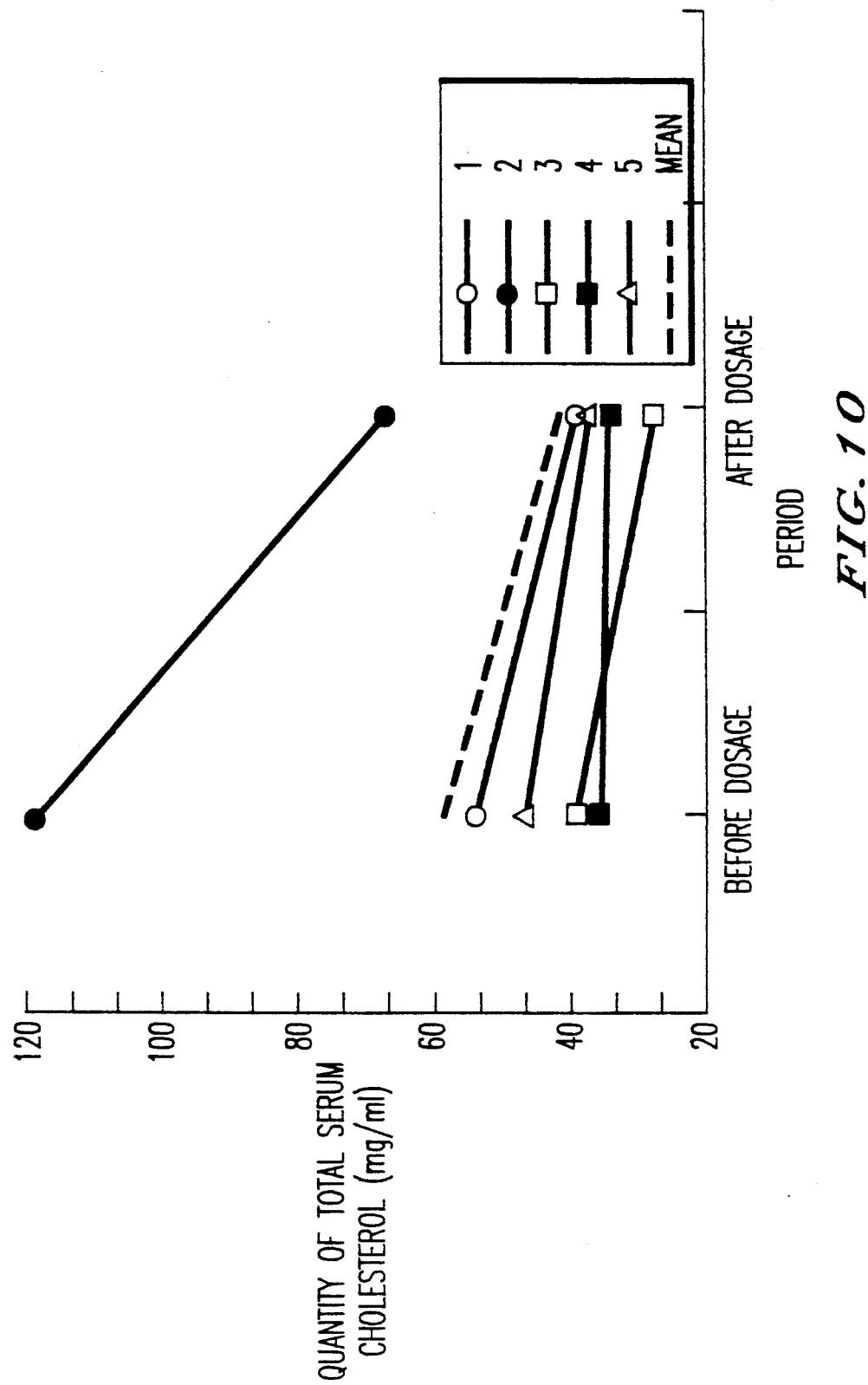

Now the present invention will be described in further detail with reference to the accompanying drawings in which:

FIG. 1 is a graph showing myeloblast and leukocyte counts in peripheral blood of patients suffering from MDS after dosage of an hM-CSF preparation of the invention, FIG. 2 is a graph showing normal leukocyte, normal neutrophil leukocyte and normal erythrocyte counts in a patient suffering from pediatric MDS after dosage of an hM-CSF preparation of the invention, FIG. 3 is a graph showing efficacy of an hM-CSF preparation on tumoricidal activity of human monocyte, FIG. 4 is a graph showing efficacy of an hM-CSF preparation on antibody-dependent tumoricidal activity of human monocyte, FIG. 5 is a graph showing recovery of leokocyte count by dosage of hM-CSF on mice to which CDDP was dosed, FIG. 6 is a graph showing recovery of platelet count by dosage of hM-CSF on mice to which CDDP was dosed, FIG. 7 is a graph showing decrease in total serum cholesterol level of a patient suffering from hyperlipemia by dosage of hM-CSF, FIG. 8 is a graph showing decrease in total serum cholesterol level of another patient suffering hyperlipemia by dosage of hM-CSF, FIGS. 9a and 9b are a graph showing the change of total serum cholesterol levels of hyperlipemia rabbits in percent before and after dosage of an hM-CSF preparation, and FIG. 10 is a graph showing the change in total serum cholesterol levels of rabbits before and after dosage of an hM-CSF preparation.

In accordance with the present invention, it has been confirmed that dosage of hM-CSF inclusive of human urinary M-CSF and rhM-CSF to patients suffering from MDS is effective not only to decrease myeloblast count in peripheral blood and to decrease in proportion of myeloblasts to total bone marrow cells, but also effective to increase erythrocyte, leukocyte and neutrophil leukocyte counts in peripheral blood of the patients.

In accordance with the present invention, it is also confirmed that human urinary M-CSF is effective to significantly augment tumoricidal activity of human monocytes and to inhibit proliferation of human cervical cancer cells. Therefore, human urinary M-CSF is effective in therapy against various malignant tumors on the hematopoietic organs and various organs, for example, myelogeneous leukemia and uterine cancer.

It is also confirmed that hM-CSF may significantly augment antibody dependent cell-mediated cytotoxicity (ADCC) of human monocytes. Therefore, hM-CSF is effective, when used in conjunction with specific antimalignant tumor antibody, to augment therapeutic effect expected from single use of hM-CSF.

In accordance with the present invention, hM-CSF can be dosed immediately after or in pallarel with the dosage of anticancer preparations containing platinum complex compounds, to eliminate or inhibit manifestation of side effects such as various troubles on hematopoietic organs and other organs and toxicity thereto.

In accordance with the present invention, it has been found that hM-CSF is effective to decrease in blood cholesterol level and neutral fats level.

Dosage of hM-CSF varies depending upon the ages and conditions of the patients, typical dosages are as follows:

(1) AGAINST MYELODISPLASTIC SYNDROME 0.4 μg–16 μg/kg (body weight)/day, preferablly
1.6 μg–8 μg/kg (body weight)/day

(2) AGAINST MALIGNANT TUMORS 0.4 μg–16 μg/kg/day [$4\times10^4 - 160\times10^4$ U/kg (body weight)/day], preferablly
1.6 μg–8 μg/kg/day [$16\times10^4 - 80\times10^4$ U/kg (body weight)/day]

(3) AGAINST SIDE EFFECTS RESULTING FROM ANTI-CANCER PREPARATIONS CONTAINING PLATINUM COMPLEX COMPOUNDS

Although cis-diammine dichlrolo platinum (cisplatin, CDDP) is a typical platinum-complex compound anticancer preparation, carboplatin (CBDA), 254-S and spiloplatin (DACCP) are also known. Dosage of these chemotherapeutic preparations may vary depending upon the ages and conditions of patients, typical dosage is 15–35 mg/mm$^2$ (area of body surface). Typical dosage of hM-CSF as an auxiliary preparation in relation with the dosage of these plutinum complex preparations are as follows:

0.4–16 μg/kg [$4\times10^4$ U – $160\times10^4$ U/kg (body weight)/day], preferablly
1.6–8 μg/kg [$16\times10^4$ U – $80\times10^4$ U/kg (body weight)/day]

(4) AGAINST HYPERLIPEMIA 0.4 μg–16 μg/kg (body weight)/day, preferablly
1.6 μg–8 μg/kg (body weight)/day Now some examples of the present invention will be described hereunder for better understanding of the present invention.

EXAMPLE 1

Therapeutic Effects Against Myelodisplastic Syndrome

(1) PREPARATION OF hM-CSF FOR MDS TREATMENT IN ACCORDANCE WITH THE PRESENT INVENTION

Added different quanties of stabilizing agents as shown in Table 1 and hM-CSF (prepared in accordance with aforementioned [PREPARATION OF HUMAN M-CSF, #2]) to 20 mM phosphate buffer solution (pH 7.2), solutions for test samples and control samples were prepared. The concentration of hM-CSF in all the solutions was 100 μg/ml. Each of the solutions was sterilized through a nitrocellulose membrane filter, 1 ml aliquot of the resultant filtrate was aseptically dispenced into a vial, freeze-dried, and then seald air-tightly to thereby obtain a plurality of products for each sample.

(2) STABILITY OF BIOLOGICAL ACTIVITY OF THE SAMPLES

Stability of biological activity of the samples was measured by conventional soft-agar-culture method using murine bone marrow cells. The results are also shown in Table 1.

As will be seen from Table 1, biological activities, after preservation at 40° C. for 3 months, in those samples containing the surface active agent (Tween 80, Trademark) in a concentration equal to or more than 10 μg/ml, or containing human serum albumine or gelatin in a concentration equal to or more than 1 mg/ml were maintained at 70% or more of those immediately after preparation of the samples.

TABLE 1

| stabilizing agent & concentration (mg/ml) | | biological activity (%) |  |
|---|---|---|---|
| | | after 1 month at 40° C. | after 3 months at 40° C. |
| Tween 80 | 0.001 | 73 | 40 |
| | 0.010 | 93 | 74 |
| | 0.100 | 85 | 89 |
| human seru albumine | 0.5 | 69 | 49 |
| | 1.0 | 87 | 71 |
| | 5.0 | 89 | 93 |
| | 10.0 | 97 | 98 |
| gelatin | 0.5 | 63 | 36 |
| | 1.0 | 81 | 70 |
| | 5.0 | 81 | 77 |
| | 10.0 | 92 | 87 |
| nil | — | 43 | 18 |

(3) THERAPEUTIC EFFECT ON MYELODISPLASTIC SYNDROME

Therapeutic effect of the samples on a patient suffering from MDS was evaluated by measurement of changes in hematological parameters, such as myeloblast, normal leukocyte, normal erythrocyte counts in the peripheral blood of the patient.

To the patient of 40 years old, the preparation in accordance with the present invention, which was prepared in the same manner as described in (1) of Example 1 and was dissolved in physiological saline solution, was daily injected by intravenous drip infusion for 14 consecutive days at the dosage of 1.6 μg of hM-CSF/kg/day.

After initiation of infusion, myeloblast and leukocyte counts in peripheral blood of the patient were periodically measured. The results are shown in FIG. 1, wherein the abscissa denotes the period shown by days, the ordinate denotes respectively peripheral blood myeloblast count with ●—●(right ordinate), and peripheral blood normal leukocyte count with ○—○, and normal neutrophil leukocyte count with △—△ (left ordinate) respectively.

As will be seen from FIG. 1, myeloblast count ●—● in the peripheral blood before initiation of infusion was 100/mm$^3$, it was decreased to 40/mm$^3$ on the 10th day, and to 10/mm$^3$ on the 30th day after initiation of infusion. Observation was continued until 100th day after initiation of infusion, and confirmed that myeloblast count was kept at 0/mm$^3$.

Meanwhile, normal leukocyte (○—○) and neutrophil leukocyte (△—△) counts in the peripheral blood before initiation of infusion were 700/mm$^3$ and 500/mm$^3$ respectively which were abnormally decreased state of leukocyte count, but they were increased, after initiation of dosage, to 750/mm$^3$ and 500/mm$^3$ on day 10 respectively, to 900/mm$^3$ and 600/mm$^3$ on day 30 respectively, and on day 90 they recovered almost their normal values, 1800/mm$^3$ and 900/mm$^3$ respectively.

It will be understood that the preparation in accordance with the present invention is effective against MDS.

EXAMPLE 2

Therapeutic Effect on Pediatric MDS

Clinical study was conducted on therapeutic effects of the preparation used in Example 1 on pediatric MDS.

To a 3 years old patient suffering from MDS whose parents gave the informed consent, the same preparation as used in Example 1 was daily injected by intravenous drip infusion for 9 consecutive days at the dosage of 2.4 μg of hM-CSF/kg/day as the effective component.

Normal leukocyte, normal neutrophil leukocyte and normal erythrocyte counts in the peripheral blood after initiation of infusion and ratio of myeloblasts to total bone marrow cells before and after initiation of infusion were periodically measured. The results are shown in FIG. 2, wherein the abscissa denotes the period shown by days, the ordinates denote respectively peripheral blood leukocyte count with ○—○, peripheral blood normal neutrophil leukocyte count with Δ—Δ (left ordinate), and peripheral blood erythrocyte count with □—□ (right ordinate).

As will be seen from FIG. 2, normal erythrocyte count (□—□) in the peripheral blood before initiation of infusion was $184 \times 10^4/mm^3$, normal leukocyte count (○—○) was $2000/mm^3$ and normal neutrophile neutrophil leukocyte count (Δ—Δ) was $180/mm^3$ respectively, they were increased, after initiation of infusion, to $208 \times 10^4/mm^3$ (normal erythrocytes), $2600/mm^3$ (normal leukocytes) and $290/mm^3$ (neutrophil leukocytes) on the 5th day, and on the 10th day they were increased to $308 \times 10^4/mm^3$ (normal erythrocytes), $3100/mm^3$ (normal leukocytes) and $530/mm^3$ (normal neutrophil leukocytes). The ratio of myeloblast count to total bone marrow cells before initiation of infusion was 23% as shown by segmental graph on left side of FIG. 2, and after initiation of infusion it was remakablly decreased to 7% as shown on right side in FIG. 2 respectively.

It will be understood that the preparation in accordance with the present invention is effective against MDS.

EXAMPLE 3

Therapeutic Effect on Malignant Tumors

Human urinary M-CSF prepared in accordance with the aforementioned [PREPARATION OF HUMAN M-CSF, #1] was used in this example. The hM-CSF was dissolved in 20 mM phosphate buffer solution (pH 7.2) together with different quantities of proteins as shown in Table 2 to prepare solutions of hM-CSF in the same concentration of 10 μg/ml for test and control samples. Each of the resultant solutions was sterilized through nitrosellulose membrane filter, 1 ml aliquot of the resultant filtrate was aseptically dispenced into a vial, and then sealed air-tightly without lyophilization thereby obtained a plurality products for each sample.

Stability of human urinary M-CSF activity and function of hM-CSF to augment tumoricidal activity of human monocytes were studied using the resultant products.

The stability of hM-CSF preparation containing human urinary M-CSF was evaluated by measuring its biological activity in conventional soft-agar-culture method using murine bone marrow cells. Studies on tumoricidal activity with respect to human monocytes was conducted using those samples which were stable for long time in the above mentioned stability test.

The results of the stability test are shown in Table 2. As will be seen from Table 2, biological activity, after preservation for 3 months from their preparation at 4° C., in those samples in which 1 mg/ml or more of human serum albumine or gelatine was added were kept at 70% or more of those immediately after preparation of the samples. That is, the biological activity of those samples in which 1 mg/ml or more of human serum albumine or gelatine was added were stable and available for clinical use.

TABLE 2

| protein & quantity added (mg/ml) | (mg/ml) | biological activity (%) 1 month at 4° C. | 3 months at 4° C. |
|---|---|---|---|
| human serum albumin | 0.5 | 85 | 68 |
|  | 1.0 | 90 | 95 |
|  | 2.5 | 98 | 97 |
|  | 5.0 | 98 | 99 |
|  | 10.0 | 99 | 98 |
| gelatine | 0.5 | 81 | 65 |
|  | 1.0 | 91 | 80 |
|  | 2.5 | 92 | 85 |
|  | 5.0 | 91 | 85 |
| nil | — | 75 | 55 |

Accordingly, it will be understood that when proteins were added more than 100 folds (weight) to human urinary M-CSF, stability of the biological activity in liquid state was improved.

The influence of said anti-tumor preparations, which was added with 5.0 mg/ml of human serum albumine as a stabilizer, to tumoricidal activity of human monocytes was measured by the method described hereunder. Human monocytes were harvested from peripheral blood of healthy men by means of Ficoll centrifugation, and a plastic adhesion method (monocyte population was more than 90% of total cells). The isolated monocytes were suspended in RPMI 1640 medium ($10^5$/ml) containing 20% of fetal calf serum, and added with the anti-tumor preparation in different concentrations of hM-CSF at 0 ng/ml (control), 25 ng/ml, 50 ng/ml and 150 ng/ml. The mixtures were incubated at 37° C. for two days, then human monocytes were washed with RPMI 1640 medium and collected. A 0.1 ml aliquot of resultant suspension containing $10^6$/ml of the monocytes was inoculated into each well of microplate having 96 wells, and then suspension of human myelogeneous leukemia cells (K-562 cells), labeled with $^{51}Cr$, in the concentration of $10^5$/ml was inoculated in the quantity of 100 μl per well. After incubation at 37° C. for 12 hours, radioactivity of free $^{51}Cr$ in supernatant of each well was measured and then tumoricidal activity was calculated therefrom in accordance with the following formula.

$$\frac{\text{activity of free }^{51}Cr}{\text{activity of total }^{51}Cr} \times 100 = \text{tumoricidal activity (\%)}$$

The results are shown in FIG. 3. As will be seen from FIG. 3, monocytes incubated under the presence of anti-tumor preparation showed significantly augmented tumoricidal activity of monocytes than those incubated under absence of anti-tumor preparation. It was found that the effect of hM-CSF on the augmentation of tumoricidal activity of monocytes shows a dose-response manner.

In FIG. 3, mean values and standard deviations of the results of the tests, which were concurrently conducted, are shown wherein the value of 100 means complete killing of tumor cells.

EXAMPLE 4

Efficacy of the Preparation on Antibody-Dependent Cell-Mediated Cytotoxicity of Human Monocytes A plurality of solutions wherein different quantities of proteins as shown in Table 3 and 10 µg/ml of human urinary M-CSF were included therein were prepared in the same manner as in Example 3. Each of the solution was subjected to sterile membrane filtration, the resultant filtrate was dispenced into vials by 1 ml each, and freezedried, then sealed to prepare anti-tumor preparations (test samples). Evaluation on the preservation stability of hM-CSF activity and augmentation effects of anticancer preparations on antibody-dependent cell-mediated cytotoxicity (ADCC) of human monocytes were carried out.

The stability was measured by soft-agar-culture method using murine bone marrow cells as in the same manner in Example 1.

The studies on the augmentation efficacy upon ADCC of human monocytes were conducted only on those preparations which were stable in the preservation test.

The results are shown in Table 3. As will be seen from Table 3, the biological activities of the preparations in which 1 mg/ml or more of human serum albumine or gelatine was added were kept more than 70% even after preservation at 40° C. for 3 months, and found to be stable.

In other words, it was confirmed that stability can be provided when proteins are added more than 100 fold to hM-CSF.

TABLE 3

| protein added | quantity added (mg/ml) | biological activity (%) 1 month at 40° C. | 3 months at 40° C. |
| --- | --- | --- | --- |
| human serum albumin | 0.5 | 73 | 55 |
|  | 1.0 | 80 | 73 |
|  | 2.5 | 88 | 90 |
|  | 5.0 | 98 | 85 |
|  | 10.0 | 99 | 92 |
| gelatine | 0.5 | 71 | 45 |
|  | 1.0 | 80 | 70 |
|  | 2.5 | 85 | 70 |
|  | 5.0 | 81 | 82 |
|  | 10.0 | 92 | 87 |
| nil | — | 45 | 20 |

The efficacy of the preparations to ADCC on human monocytes were studied in the manner described hereunder:

The anticancer preparations including 5.0 mg/ml of gelatin in Table 3 were used. As in the same manner in Example 3, anti-tumor preparations were respectively added to human monocytes, the resulted solutions were incubated for 2 days in the respective culture medium, then washed to collect human monocytes. Into each well of 96 wells microplate, monocytes suspension in $10^6$/ml concentration was inoculated 100 µl each. Into each well, Raji cells originating from human lymphoma and the anti-Raji cell specific antibody were respectively inoculated in the concentration of 0 µg/ml (control), 1 µg/ml or 10 µg/ml and incubated respectively. After 12 hours incubation, the respective supernatant were measued for free $^{51}Cr$ radioactivity, and calculated tumoricidal activity thereof in the same manner as in Example 3. The results are shown in FIG. 4.

As will be seen from FIG. 4, significant augmentation of ADCC was observed for the monocytes which were incubated under the presence of anti-tumor preparations as well as anti-tumor antibody in comparison with those under absence thereof. The augmentative efficay was linearly proportional to the concentarations of human urinary M-CSF, which is the effective component of the preparations, and the specific antibody.

In FIG. 4, the mean values and the standard deviations of the values, resulted from concurrently conducted experiments, are shown wherein the value of 100 means 100% of tumor cells were killed.

EXAMPLE 5

Efficacy of Anti-Tumor Preparations Against Proliferation of Human Cervical Cancer Cells BALB/C nude mice were divided into 3 groups (10 mice/group) and they were subcutaneously transplanted $10^5$ of human cervical cancer cells (Hela cells) respectively. The anti-tumor preparation of Example 3 was intrapenetoneally dosed to the mice every day for 7 consecutive days from the next day of the transplantation in the different dosage at 4.0 µg/kg body weight ($40 \times 10^4$ U/kg body weight), 16 µg/kg body weight ($160 \times 40^4$ U/kg), 64 µg/kg body weight ($640 \times 10^4$ U/kg). On the 28th day after the transplantation, tumors were enucleated and weighed to thereby anti-tumor activities were measured. The results are shown in Tbale 4.

As will be seen from Table 4, minimization of tumors were apparently observed for the mice to which more than 16 µg/kg ($160 \times 10^4$ U/kg body weight) of anti-tumor preparations were dosed, and concluded that the preparations have anti-tumor activity.

TABLE 4

| dosage ($\times$ µg/kg) | total weight of tumors (mg) |
| --- | --- |
| 0 (control) | 725 ± 150 |
| 4.0 | 638 ± 180 |
| 16.0 | 480 ± 95 |
| 64.0 | 395 ± 110 |

EXAMPLE 6

Efficacy of Human M-CSF on Presentation of Fc Receptors on Human Monocytes

The human monocytes isolated in Example 3 were incubated under the presence of and under the absence of anti-tumor preparations respectively for 2 days, each of the resultant cultures was mixed with sheep erythrocytes which were previously coated with rabbit IgG. The resultant mixtures were sufficiently washed, then the erythrocytes which combined with monocytes were counted for judgement of presentation of Fc receptors. The results are shown in Table 5.

As will be seen from Table 5, apparently a large number of erythrocytes were combined to monocytes which were incubated under the presence of anti-tumor preparations.

From the results of Example 6, it was found that human urinary M-CSF augmented ADCC activity of human monocytes. It is assumed that the results are derived from acceleration of Fc-receptor-presentation on monocytes by the anti-tumor preparations and strengthened bonding of monocytes to the target tumor cells.

TABLE 5

| [EFFICACY OF HUMAN M-CSF IN PRESENTATION OF Fc RECEPTORS ON HUMAN MONOCYTES] | | | |
|---|---|---|---|
| human urinary M-CSF (ng/ml) | 0 | 25 | 50 |
| erythrocytes/monocytes | 1.5 ± 2.0 | 3.1 ± 2.4 | 5.0 ± 3.2 |

In Table 5, values are shown with the mean values and standard deviations as counted erythrocytes which combined with monocytes among 100 monocytes.

EXAMPLE 7

Efficacy of Human M-CSF to Reduce Acute Toxicities of Anti-Tumor Preparations Containing Platinum-Complex Compound (1) Preparation of Auxiliary Preparations To 20 mM phosphate buffer solution, human urinary M-CSF and proteins in different quantities as shown in Table 6 were added to prepare 10 µg/ml hM-CSF solution. The resultant solutions were subjected to nitrocellulose sterile membrane filtaration, and the resultant filtrates were aseptically dispenced into vials by 1 ml each, then airtightly sealed to prepare auxiliary preparations.

(2) Stability of Biological Activity of Auxiliary Preparations

The stability of auxiliary preparations of the present invention were evaluated by measurement of M-CSF activity utilizing soft agar culture method with murine bone marrow cells. The results are shown in Table 6.

As will be seen from Table 6, the biological activity of the auxiliary preparations in which more than 1 mg/ml of human serum albumine or gelatine was added were kept more than 70% of those at the initiation of this experiments (immediately after preparation of the auxiliary preparations) even after 3 months preservation at 4° C., and the auxiliary preparations were found to be stable.

TABLE 6

| protein | | biological activity (%) | |
|---|---|---|---|
| protein added | quantity (mg/ml) | after 7 days at 4° C. | after 3 months at 4° C. |
| human serum albumine | 0.5 | 85 | 68 |
| | 1.0 | 90 | 95 |
| | 2.5 | 98 | 97 |
| | 5.0 | 98 | 99 |
| | 10.0 | 99 | 98 |
| gelatin | 0.5 | 81 | 65 |
| | 1.0 | 91 | 80 |
| | 2.5 | 92 | 85 |
| | 5.0 | 91 | 85 |
| | 10.0 | 90 | 89 |
| nil | — | 75 | 55 |

(3) Efficacy of the Auxiliary Preparations for Reducing Acute Toxicity

Normal C₃H/HeN mice were divided into 4 groups (10 mice/group) and 19 mg/kg of CDDP (a quantity corresponding to LD$_{50}$) was intra-pentoneally administered in all mice. To each mice, the auxiliary preparation, which contained 5.0 mg/ml of human serum albumine, in different quantities as shown in Table 7 was intravenously injected every day from the next day of initiation of this test for 5 consecutive days, and mortality rate of the mice within 7 days after the initiation of this test was observed. The results are shown in Table 7.

As will be seen from Table 7, the mortality rate was remarkably decreased by the dosage of the auxiliary preparation, in other words, the acute toxicity of the platinum-complex anti-tumor preparation was reduced or compensated. Also it is observed that the decrease of mortality rate directly proportional to the dosage of the auxiliary preparation.

TABLE 7

| dosage of auxiliary preparation (µg/kg) | died mice/test mice (mortality rate %) | |
|---|---|---|
| | after 4 days | after 7 days |
| control group 0 | 4/10 (40%) | 10/10 (100%) |
| test group 10 | 0/10 (0%) | 8/10 (80%) |
| test group 50 | 0/10 (0%) | 5/10 (50%) |
| test group 100 | 0/10 (0%) | 4/10 (40%) |

From the results, it was confirmed that hM-CSF is effective for reducing acute toxicity of the platinum-complex anticancer preparation when hM-CSF is injected concurrently therewith.

EXAMPLE 8

Efficacy Against Disorders on Hematopoietic Organs and Renal Injury Resulted from Dosage of Platinum-Complex Anti-Tumor Preparation Among the auxiliary preparations in Example 7, only the one which contain 5 mg/ml of gelatine was used in this experiment.

To all the C₃H/HeN mice divided into 2 groups each consisting of 5 mice, cisplatin (CDDP), platinum-complex anti-tumor preparation, was intrapenetoneally injected every day for two days in the dosage of 4 mg/kg body weight/day. To the mice belonging to the first group (test group), the auxiliary preparation containing 5 mg/ml of gelatine was dosed in the dosage of 32 µg/kg (320×10⁴ U/kg body weight) for 5 consecutive days once a day initiating from the next day after the dosage of CDDP. To all the mice belonging to the second group (control group), no auxiliary preparation was dosed. The efficacy against disorders in hematopoietic organs and renal injuy was periodically evaluated by leukocyte and platelet counts in the peripheral blood, and serum BUN (blood uria nitrogen) and creatinine levels on the 1st, 3rd, 5th, 7th, 9th, 11th and 14th days from the next day of the last dosage of CDDP.

The results are shown in FIGS. 5 and 6 as well as Table 8.

In FIG. 5, the abscissa denotes the period with days after the last dosage of CDDP, the ordinate indicates leukocytes count ($\times 10^2$/mm³), and the curve ○—○ indicates the values of test group to which the auxiliary preparation was dosed and ●—● indicates the values of control group to which no auxiliary preparation was dosed respectively.

In FIG. 6, abscissa denotes the period shown by days after the last dosage of CDDP, the ordinate denotes platlets count ($\times 10^4$/mm³), and the curve ○—○ indicates the values of test group to which the auxiliary preparation was dosed and ●—● indicates the values of control group to which no auxiliary preparation was dosed respectively.

In the both figures, the asterisks (*) denote that the values are significant differences of 5%.

It will be understood that dosage of the auxiliary preparation may counteract against decrease in peripheral blood leukocytes and platelets counts, and may accelerate the recovery of their normal counts of the mice to which the auxiliary preparation was dosed compared with those to which no auxiliary preparation was dosed. Thus the efficacy of hM-CSF against disorder on the hematopoietic organs is confirmed. It will be also understood from Table 8 that increase in serum BUN and creatinine levels are milder for the mice to which the auxiliary preparation was dosed than those not dosed, thus it is confirmed that hM-CSF is effective against renal injuly caused by the platinum-complex anti-tumor preparations.

TABLE 8

| days after CDDP dosing | BUN (mg/dl) | | creatinine (mg/dl) | |
|---|---|---|---|---|
| | cont. grp. | test grp. | cont. grp. | test grp. |
| 0 | 14.6 ± 1.2 | 14.6 ± 1.2 | 0.67 ± 0.04 | 0.67 ± 0.04 |
| 5 | 21.9 ± 3.9 | 16.8 ± 1.9 | 1.17 ± 0.08 | 0.79 ± 0.06 |
| 14 | 24.0 ± 3.9 | 16.9 ± 2.6 | 1.08 ± 0.03 | 0.76 ± 0.09 |

EXAMPLE 9

Efficacy of Human M-CSF For Decrease of Cholesterol Level on the Patients Having Hyperlipemia (1) Preparation of Anti-Hyperlipemia Preparation To 20 mM phosphate buffer solution of pH 7.2, hM-CSF prepared in accordance with [PREPARATION OF HUMAN M-CSF, #1] described hereinbefore and stabilizing agnet in different concentrations as shown in Table 9 were added to prepare solutions of hM-CSF in the concentration of 100 µg/ml. Each of the resultant solutions was subjected to nitrocellulose sterile membrane filtration, the resultant filtrates were aseptically dispenced into vials by 1 ml each, the freezedried to obtain anti-hyperlipemia preparations in accordance with the present invention.

(2) Stability of Biological Activity of the Preparations

The stability of hM-CSF activity in the preparations were measured using soft agar culture method with murine bone marrow cells. The results are shown in Table 9. As will be seen from Table 9, the biological activities of the preparations in which more than 10 µg/ml of Tween 80 or more than 1 mg/ml of human serum albumine or gelatine were added were kept over 70% to those immediately after preparation thereof, even after 3 months preservation period at 40° C., and it was confirmed that these preparations were stable.

TABLE 9

| stabilizer & concentration (mg/ml) | biological activities (%) | |
|---|---|---|
| | 1 month at 40° C. | 3 months at 40° C. |
| TOWEEN-80 0.001 | 78 | 51 |
| 0.010 | 98 | 98 |
| 0.100 | 87 | 93 |
| human serum 0.5 | 73 | 55 |
| 1.0 | 88 | 73 |
| 5.0 | 98 | 95 |
| 10.0 | 99 | 92 |
| gelatin 0.5 | 71 | 45 |
| 1.0 | 80 | 70 |
| 5.0 | 81 | 82 |
| 10.0 | 92 | 87 |
| nil | — | 45 | 20 |

(2) Efficacy of Anti-Hyperlipemia preparations Against Decrease in Choresterol Level An anti-hyperlipemia preparation containing 5 mg/ml of human albumine was prepared in the same manner as described in [PREPARATION OF HUMAN-CSF, #1]. To 2 patients suffering from hyperlipemia, the anti-hyperlipemia preparation was intravenously dosed every day by drip infusion for 14 consecutive days in the dosage of 1.6 µg/kg body weight/day. The efficacy for decreasing cholesterol level of the preparation was evaluated by periodical measurement thereof in the serum with 7 days interval starting on the day initiating dosage of the preparation. FIGS. 7 and 8 show the changes in blood cholestrol levels of the patients.

As will be seen from FIG. 7, the serum cholesterol level of the fisrst patient was remarkablly decreased from 395 mg/ml before initiation of dosage of the preparation to 170 mg/ml on the day after elapsing 3 weeks from the initiation of the preparation-dosage thereby normal cholesterol level was recovered. As will be noted from FIG. 8, the serum cholesterol level of the second patient was remarkablly decreased from 280 mg/ml before the initiation of dosage of the preparation to 195 mg/ml on the day after elapsing 2 weeks from the initiaion of preparation-dosage. In the both figures, the abscissas denote the period presented by days and the ordinates denote the total serum cholesterol levels (mg/ml).

From the results, it was confirmed that hM-CSF is effective against hyperlipemia, and thus against arteriosclerosis derived from hyperlipemia.

EXAMPLE 10

Efficacy for Decreasing Serum Cholesterol Levels of Model Animals of Hyperlipemia The efficacy of the anti-hyperlipemia preparations of the present invention to decrease cholesterol and neutral fats levels on model animals of hyperlipemia were evaluated using similar preparations used in Example 9, except that 20 µg/ml of Tween 80 as the stabilizer was used.

All the healthy Sprague-Dawley rats divided into 2 groups each consisting of 5 were prelimiarily bred for 1 month with feeding fat-rich feed. To all rats belonging to the first group (test group), the preparation was intravenously infused every day for 7 consecutive days at the dosage of 16 µg/kg body weight/day. To all rats belonging to the second group (control group), only the same buffer solution which was used for preparation of the anti-hyperlipemia preparation was dosed in the same manner and at the same dosage as in the test group. The serum cholesterol and neutral fats levels of all the rats were periodically measured. The results are shown in Table 10.

As will be seen from Table 10, the serum cholesterol and neutral fats levels were remarkably decreased by the dosage of the preparation. Thus it was apparently exemplefied that hM-CSF is effective as a therapeutic preparation against hyperlipemia and arteriosclerosis derived therefrom.

TABLE 10

| days from the initiation of dosage | total cholesterol (mg/ml) control | total cholesterol (mg/ml) test | neutral fats (mg/ml) control | neutral fats (mg/ml) test |
|---|---|---|---|---|
| 0 | 235 | 235 | 126 | 126 |
| 5 | 243 | 178 | 136 | 89 |
| 10 | 219 | 162 | 114 | 86 |
| 15 | 229 | 185 | 123 | 93 |

EXAMPLE 11

Efficacy of rhM-CSF for Serum Cholesterol Level on Hyperlipemia Model Animals (1) Preparation of Anti-Hyperlipemia Preparations To 20 mM phosphate buffer solution of pH 7.2 including 0.15M sodium chloride, 10 mg/ml of mannitol or mannit and a quantity of rhM-CSF were added to prepare rhM-CSF solution in the concentration of 100 μg/ml. The resultant solution was subjected to nitrocellulose sterile membrane filtration, the resultant filtrate was aseptically dispenced into vials by 1 ml each to thereby obtain therapeutic preparation products.

(2) Effect of Decreasing Cholesterol Level Against Hyperlipemia Model Animals

The efficacy of rhM-CSF for decreasing serum cholesterol levels of hyperlipemia rabbits (Watanabe rabbits) was evaluated. To the 4 rabbits, 2.5 ml of the buffer solution which was used for preparation of the therapeutic preparation was subcutaneously infused every day for 7 consecutive days, therafter observed for 10 days after the last day of the infusion (control period). Subsequently, the therapeutic preparation was subcutaneously infused every day for 7 consecutive days at the dosage of 50 μg/day, then observed for 8 days after the last day of the infusion of the preparation (test period). The serum cholesterol level during the control and test periods were periodically measured, the decreasing rate of the cholesterol level during the test period to that during the control period was calculated. The results are shown in FIG. 9.

As will be seen from FIG. 9, the cholesterol levels during control period were maintained within the range of 105%–97% to that before initiation of the dosage of the control preparation (buffer solution), that is there was no significant change in the values during the control period. On the other hand, the serum cholesterol levels during the test period were remarkably decreased to 83%–85% to those before the initiation of this test. In FIG. 9, the abscissa denotes the period presented by days and the ordinate denotes the total cholesterol level (mg/ml) in percent. From the results, it was cralified that rhM-CSF is effective against hyperlipemia as well as arteriosclerosis resulted therefrom.

EXAMPLE 12

Efficacy of rhM-CSF for Decreasing Cholesterol Level of Normal Healthy Animals

An rhM-CSF preparation containing 5 mg/ml of human serum albumin was prepared in the same manner as in Example 11 using the same buffer solution. To 5 NewZeeland White rabbit, the preparation was subcutaneously dosed every day for 7 consecutive days at the dosage of 50 μg/kg body weight, then the serum cholesterol levels before and after dosage were observed. The results are shown in FIG. 10. In FIG. 10, the abscissa denotes period and the ordinate denotes total serum cholesterol level (mg/ml).

As will be seen from FIG. 10, dosage of the preparation may result in decrease of serum cholesterol levels, and the effects are remarkable in the animals having higher cholesterol levels before the dosage of the preparation and lesser in those having lower cholesterol levels. The mean drop in the serum cholesterol levels was 28% of that before the dosage of the preparation. From the results, it was clarified that rhM-CSF is effective against hyperlipemia as well as arteriosclerosis derived therefrom.

It will be apparent from the foregoing examples that the present invention provides therapeutic preparations against MDS which had been difficult to cure. The anti-MDS preparations of the present invention can reduce or disperse myeloblasts and increase normal peripheral blood cells.

It will be understood that the present invention provides therapeutic preparations which have remarkable anticancer activity and which have no severe side effects. The anticancer preparations of the present invention are effective for therapy against malignant tumor by it self and are also effective thereto when they are dosed together with specific antibody against malignant tumors concerned.

It will be apparent that the present invention provides auxiliary preparations to be dosed thogether with platinum-complex anti-tumor preparations. The auxiliary preparations of the present invention can reduce or minimize side effects and troubles on kidneies and/or hematopoietic organs caused by the platinum-complex anticancer preparations.

It will be also apparent that the present invention provides therapeutic preparations against hyperlipemia and arteriosclerosis. The anti-hyperlipemia preparations of the present invention can remarkably decrease cholesterol and neutral fats levels in the peripheral blood without no severe side effects, thus they are effective for prevention and therapy against hyperlipemia and arteriosclerosis resulted therefrom.

It will be further understood that the present invention provides therapeutic preparations containing rhM-CSF against hyperlipemia and asteosclerosis. The anti-hyperlipemia preparations of the present invention can remarkably decrease cholesterol and neutral fats levels in the peripheral blood without no severe side effets, thus they are effective for prevention and therapy against hyperlipemia and arteriosclerosis resulted therefrom.

It will be also understtod that the present invention provides therapeutic preparations having stable biological activities of hM-CSF by addition of one or more of stabilizers selected from the group consisting of surface active agents, human serum albumin and gelatine.

What is claimed is:

1. A method of treating myelodysplastic syndrome, comprising administering to a person in need thereof an effective amount of naturally-occurring human monocyte-macrophage colony stimulating factor.

2. The method of claim 1, wherein 0.4–16 μg/kg body weight/day of said colony stimulating factor is administered.

3. The method of claim 1, wherein 1.6–8 μg/kg body weight/day of said colony stimulating factor is administered.

4. A method of decreasing myeloblast count in peripheral blood and for decreasing the proportion of myeloblasts to total bone marrow cells while increasing erythrocyte, leukocyte and neutrophil leukocyte counts in peripheral blood, comprising administering to a patient having myelodysplastic syndrome an effective amount of naturally-occurring human monocyte-macrophage colony stimulating factor.

5. The method of claim 4, wherein 0.4–16 µg/kg body weight/day of said colony stimulating factor is administered.

6. The method of claim 4, wherein 1.6–8 µg/kg body weight/day of said colony stimulating factor is administered.

7. The method of claim 4, wherein one or more stabilizers selected from the group consisting of human serum albumin, polyoxyethylenesorbitan monooleate and gelatin is administered with said colony stimulating factor.

8. The method of claim 1, wherein one or more stabilizers selected from the group consisting of human serum albumin, polyoxyethylenesorbitan monooleate and gelatin is administered with said colony stimulating factor.

* * * * *